United States Patent
Katscher et al.

(10) Patent No.: US 10,330,757 B2
(45) Date of Patent: Jun. 25, 2019

(54) MRI METHOD FOR CALCULATING DERIVED VALUES FROM B0 AND B1 MAPS

(71) Applicant: KONINKLIJKE PHILIPS N.V., Eindhoven (NL)

(72) Inventors: Ulrich Katscher, Eindhoven (NL); Jan Jakob Meineke, Eindhoven (NL); Holger Eggers, Eindhoven (NL); Peter Boernert, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 81 days.

(21) Appl. No.: 15/544,397

(22) PCT Filed: Jan. 21, 2016

(86) PCT No.: PCT/EP2016/051199
§ 371 (c)(1),
(2) Date: Jul. 18, 2017

(87) PCT Pub. No.: WO2016/116545
PCT Pub. Date: Jul. 28, 2016

(65) Prior Publication Data
US 2018/0011158 A1    Jan. 11, 2018

Related U.S. Application Data

(60) Provisional application No. 62/138,492, filed on Mar. 26, 2015.

(30) Foreign Application Priority Data

Jan. 21, 2015 (EP) .................................. 15151936

(51) Int. Cl.
*G01R 33/44* (2006.01)
*A61B 5/055* (2006.01)
(Continued)

(52) U.S. Cl.
CPC ............ *G01R 33/443* (2013.01); *A61B 5/055* (2013.01); *G01R 33/243* (2013.01);
(Continued)

(58) Field of Classification Search
CPC .. G01R 33/443; G01R 33/243; G01R 33/246; G01R 33/4816; G01R 33/4824; G01R 33/4828; G01R 33/54; A01B 5/055
See application file for complete search history.

(56) References Cited

U.S. PATENT DOCUMENTS 5,995,863 A    11/1999   Farace et al.
2005/0030025 A1   2/2005   Ma et al.
(Continued)

FOREIGN PATENT DOCUMENTS

WO    2014154728 A1    10/2014

OTHER PUBLICATIONS

Katscher U et al: "Determination of Electric Conductivity and Local SAR Via B1 Mapping",IEEE Transactions on Medical Imaging, IEEE Service Center, Piscataway, NJ, US, vol. 28, No. 9, Apr. 14, 2009 ,pp. 1365-1374.
(Continued)

*Primary Examiner* — Gregory H Curran

(57) ABSTRACT

The invention provides for a magnetic resonance imaging system (100, 300, 100) for acquiring magnetic resonance data (110, 1104) from a subject (118) within an imaging zone (108). The magnetic resonance imaging system comprises a memory (136) for storing machine executable instructions (160, 162, 164, 166, 316) and pulse sequence data (140, 1102). The pulse sequence data comprises instructions for controlling the magnetic resonance imaging system to acquire magnetic resonance data according to a magnetic resonance imaging method. The magnetic resonance imaging system further comprises a processor (130) for control-
(Continued)

ling the magnetic resonance imaging system. Execution of the machine executable instructions causes the processor to: acquire (1200) the magnetic resonance data by controlling the magnetic resonance imaging system with the pulse sequence data; calculate (1202) a B0 inhomogeneity map (148) by analyzing the magnetic resonance imaging data according to the magnetic resonance imaging method, calculate (1204) a B1 phase map (150) and/or a B1 amplitude map (1106) by analyzing the magnetic resonance data according to the magnetic resonance imaging method; and calculate (1206) a second derivative (1110) of the B1 phase map and/or a second derivative of the B1 magnitude map 1 and/or a second derivative of the B0 in homogeneity map in at least one predetermined direction. The second derivative is calculated using a corrected voxel size in the at least one predetermined direction, wherein the corrected voxel size is calculated using a correction factor calculated from the derivative of the B0 inhomogeneity map.

14 Claims, 10 Drawing Sheets

(51) Int. Cl.
| | | |
|---|---|---|
| *G01R 33/24* | (2006.01) | |
| *G01R 33/48* | (2006.01) | |
| *G01R 33/565* | (2006.01) | |
| *G01R 33/56* | (2006.01) | |
| *G01R 33/54* | (2006.01) | |
| *G01R 33/28* | (2006.01) | |

(52) U.S. Cl.
CPC ....... *G01R 33/246* (2013.01); *G01R 33/4816* (2013.01); *G01R 33/4824* (2013.01); *G01R 33/4828* (2013.01); *G01R 33/54* (2013.01); *G01R 33/5608* (2013.01); *G01R 33/56563* (2013.01); *G01R 33/288* (2013.01)

(56) References Cited

U.S. PATENT DOCUMENTS

| | | | |
|---|---|---|---|
| 2014/0184219 A1 | 7/2014 | Kim et al. | |
| 2014/0232393 A1* | 8/2014 | Wheaton | G01R 33/24 324/309 |
| 2015/0362575 A1* | 12/2015 | Ourselin | G01R 33/56536 382/131 |

OTHER PUBLICATIONS

Joonsung Lee et al: "Reduction of boundary artifact in electrical property mapping using MREPT", Proceedings of the International Society for Magnetic Resonance in Medicine, 21st Annual Meeting and Exhibition, Salt Lake City, Utah, USA, Apr. 20-26, 2013,vol. 21, Apr. 6, 2013 p. 4183.

E Balidemaj et al: "CSI-EPT: A novel Contrast Source Inversion approach to EPT and patient-specific SAR based on B1+ maps",Proceedings of the International Society for Magnetic Resonance in Medicine, 21st Annual Meeting and Exhibition, Salt Lake City, Utah, USA, Apr. 20-26, 2013, vol. 21, Apr. 6, 2013 (Apr. 6, 2013), p. 4185.

Dixon WT, "Simple Proton Spectroscopic Imaging" Radiology 1984; 153:p. 189-194.

Tobias Voigt et al: "Quantitative conductivity and permittivity imaging of the human brain using electric properties tomography",Magnetic Resonance in Medicine, vol. 66, No. 2,Feb. 24, 2011 (Feb. 24, 2011), pp. 456-466.

Gabriel S et al., "The Dielectric Properties of Biological Tissues . . . " Phys Med Biol 41 (1996) 2251-2269.

Stehning C et al., "Real-Time Conductivity Mapping Using Balanced SSFP and Phase Based Reconstruction" ISMRM 19 (2011) p. 128.

Coombs B D et al: "Two-Point Dixon Technique for Water-Fat Signal Decomposition With B0 Inhomogeneity Correction" Magnetic Resonance in Medicine, John Wiley & Sons, Inc, US, vol. 38, No. 6,Dec. 1, 1997 (Dec. 1, 1997), pp. 884-889.

Glover G H et al: "Three-Point Dixon Technique for True Water/Fat Decomposition With B0 Inhomogeneity Correction",Magnetic Resonance in Medicine, John Wiley & Sons, Inc, US,vol. 18, No. 2, Apr. 1, 1991 (Apr. 1, 1991),pp. 371-383.

Kay Nehrke et al: "DREAM—A novel approach for robust, ultrafast, multislice B 1mapping".Magnetic Res0nance in Medicine,vol. 68, No. 5,Jan. 17, 2012 (Jan. 17, 2012), pp. 1517-1526.

Paul S. Morgan et al: "Correction of spatial distortion in EPI due to inhomogeneous static magnetic fields using the reversed gradient method".Journal of Magnetic Resonance Imaging,vol. 19, No. 4, Jan. 1, 2004 (Jan. 1, 2004), pp. 499-507.

Lee Seung-Kyun et al: "Tissue Electrical Property Mapping From Zero Echo-Time Magnetic Resonance Imaging", IEEE Transactions on Medical Imaging, IEEE Service Center, Piscataway, NJ, US, vol. 34, No. 2,Oct. 8, 2014 (Oct. 8, 2014), pp. 541-550.

Xiaotong Zhang et al: "Complex B 1 mapping and electrical properties imaging of the human brain using a 16-channel transceiver coil at 7T",Magnetic Resonance in Medicine,vol. 69, No. 5, Jun. 12, 2012 (Jun. 12, 2012), pp. 1285-1296.

Perkins T G et al: "Preliminary Clinical Experience with a Multiecho 2-Point DIXON (mDIXON) Sequence at 3T as an Efficient Alternative for Both the SAR-intensive Acquired In-and Out-of-Phase Chemical Shift Imaging as well as for 3D Fat-suppressed T1-weighted Sequences used for Dynamic Gadolinium-enhanced Imaging", International Society for Magnetic Resonance in Medicine. Scientific Meeting and Exhibition. Proceedings, International Society for Magnetic Resonance in Medicine, US, Apr. 17, 2010 (Apr. 17, 2010) , pp. 556, XP007919293, ISSN: 1524-6965.

\* cited by examiner

MRI METHOD FOR CALCULATING DERIVED VALUES FROM B0 AND B1 MAPS

CROSS REFERENCE TO RELATED APPLICATIONS

This application is a U.S. national phase application of International Application No. PCT/EP2016/051199, filed on Jan. 21, 2016, which claims the benefit of U.S. provisional Application Ser. No. 62/138,492 and EP 15151936.0 filed Jan. 21, 2015 and is incorporated herein by reference.

TECHNICAL FIELD OF THE INVENTION

The invention relates to magnetic resonance imaging, in particular to the processing of magnetic resonance images to account for geometric distortions of voxel size.

BACKGROUND OF THE INVENTION

A large static magnetic field is used by Magnetic Resonance Imaging (MRI) scanners to align the nuclear spins of atoms as part of the procedure for producing images within the body of a patient. This large static magnetic field is referred to as the B0 field. During an MRI scan, Radio Frequency (RF) pulses generated by one or more transmitter coils cause perturbations to the local magnetic field, and RF signals emitted by the nuclear spins are detected by one or more receiver coils. These RF signals are used to construct the MR images. These coils can also be referred to as antennas. Further, the transmitter and receiver coils can also be integrated into one or more transceiver coils that perform both functions. It is understood that the use of the term transceiver coil also refers to systems where separate transmitter and receiver coils are used. The transmitted RF field is referred to as the B1 field.

MRI scanners are able to construct images of either slices or volumes. A slice is a thin volume that is only one voxel thick. A voxel is a small volume over which the MR signal is averaged, and represents the resolution of the MR image. A voxel may also be referred to as a pixel herein.

Dixon methods of magnetic resonance imaging include a family of techniques for producing separate water and lipid (fat) images. The various Dixon techniques such as, but not limited to, two-point Dixon methods, three-point Dixon methods, and multi-point Dixon methods are collectively referred to herein as Dixon techniques or methods. The terminology to describe the Dixon techniques is well known and has been the subject of many review articles and is present in standard texts on Magnetic Resonance Imaging. For example, the "Handbook of MRI Pulse Sequences" by Bernstein et al., published by Elsevier Academic Press in 2004, contains a review of some Dixon techniques on pages 857 to 887.

United States patent application US 20140184219 A1 discloses calculating a zero phase estimation of a B1 phase map using a B0 inhomogeneity map.

SUMMARY OF THE INVENTION

The invention provides for a magnetic resonance imaging system, a method of operating a magnetic resonance imaging system and a computer program product in the independent claims. Embodiments are given in the dependent claims.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the C programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, bluetooth connection, wireless local area network connection, TCP/IP connection, ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins using the antenna of a magnetic resonance apparatus during a magnetic resonance imaging scan. Magnetic resonance data is an example of medical image data. A Magnetic Resonance (MR) image is defined herein as being the reconstructed two or three dimensional visualization of anatomic data contained within the magnetic resonance imaging data. This visualization can be performed using a computer.

In one aspect an example provides for a magnetic resonance imaging system for acquiring magnetic resonance data from a subject within an imaging zone. The magnetic resonance imaging system comprises a memory for storing machine-executable instructions and Dixon pulse sequence data. Pulse sequence data as used herein encompasses data which comprises instructions for controlling a magnetic resonance imaging system or data which may be readily converted into such instructions. For example a pulse sequence is commonly a timing diagram which illustrates what components of a magnetic resonance imaging system do at a particular point in time. Such a timing diagram or data descriptive of a timing diagram could be converted into instructions for controlling the magnetic resonance imaging system.

The Dixon pulse sequence data comprises instructions for controlling the magnetic resonance imaging system to acquire magnetic resonance data according to an n-point Dixon method. n is greater than or equal to 2. A review of common Dixon techniques may for instance be found in the Handbook of MRI Pulse Sequences by Bernstein et al. (see pages 857-887).

The magnetic resonance imaging system further comprises a processor for controlling the magnetic resonance imaging system. Execution of the machine-executable instructions causes the processor to acquire magnetic resonance data by controlling the magnetic resonance imaging system using the Dixon pulse sequence data. Execution of the machine-executable instructions causes the processor to estimate a B0 inhomogeneity map and to estimate an estimated B1 phase map by analyzing the magnetic resonance data with an n-point Dixon method.

n-point Dixon methods fit a signal equation, which describes the evolution of the MR signal over time, to the Dixon pulse sequence data. The signal equation typically includes the contributions of water and fat to the MR signal as unknowns, as well as a phase offset over time common to water and fat. By contrast, the phase offset over time between water and fat due to the difference in chemical shift between water and fat is usually assumed to be known, as is the amplitude variation of the fat signal over time due to de- and rephasing of the spectral components of fat. The contributions of water and fat to the MR signal may either be considered as real variables, in which case a further unknown is introduced to characterize the phase offset common to water and fat at the time of excitation, i.e. the center of the RF pulse, or as complex variables. In the first case, the further unknown is herein called zero echo time B1 phase map $\varphi_0$. In the second case, the phase of the complex variable modeling the contribution of water to the MR signal, herein denoted by $\varphi$, is rewound to zero echo time according to $$\varphi_0 = \varphi - \gamma \Delta B_0 t,$$

where $\gamma \Delta B_0$ is the phase offset per unit time common to water and fat, and t is the first echo time, at which the Dixon pulse sequence acquired data. The latter step is for example known from the United States Patent Application US2014/0184219 A1. Similarly, the phase of the complex variable modeling the contribution of fat to the MR signal may be rewound to zero echo time, taking the additional phase offset over time between water and fat due to the difference in chemical shift between water and fat into account. Alternatively, both may be performed and the results may be suitably averaged. In more detail, The basic equation for EPT is given by (cf. Katscher U et al., IEEE Trans Med Imag, 28 (2009) 1365)

$$\frac{-\nabla^2 B_1}{\mu_0 \omega B_1} = \omega \varepsilon - i\sigma \tag{1}$$

with $\varepsilon$ the permittivity, $\sigma$ the electric conductivity, $\mu_0$ the vacuum permeability, and $\omega$ the Larmor frequency of the MR system applied. Frequently, a constant $B_1$ amplitude of the positive circular polarised RF field $B_1$ can be assumed, reducing Eq. (1) to conductivity imaging based only on the $B_1$ phase $\varphi$ (cf. Voigt T et al., MRM 66 (2011) 456)

$$\frac{\nabla^2 \varphi}{\mu_0 \omega} = \sigma. \tag{2}$$

The basic equation for Dixon methods is given by $$S_n = (W + F e^{i\vartheta_n}) e^{i\varphi_n} \tag{3}$$

with $S_n$ the measured composite signal at echo time $TE_n$, W the unknown water signal, F the unknown fat signal, $\vartheta_n$ the known phase offset between fat and water signal at $TE_n$, induced by the difference in chemical shift between fat and water, and $\varphi_n$ the unknown phase error at $TE_n$, typically induced primarily by $B_0$ inhomogeneities. the phase evolution of the Dixon scans is extrapolated/demodulated to echo time $T_E=0$. At zero echo time TE=0, the phase map is not affected by $B_0$ inhomogeneities, i.e., it represents the purely RF-related phase $\varphi$ in Eq. 2 as required by EPT to compute the electrical conductivity of the tissue.

From the Dixon scan, relative concentrations of fat $c_F(r)$ and water $c_W(r)$ are obtained. In some of the Dixon applications some care is necessary to make these numbers really quantitative (see water/fat fraction imaging), because the signal intensity might be colored by the sequence parameters used. This yields an estimation of the total conductivity $\sigma_T(r)$ via $$\sigma_T(r) \approx \sigma_F c_F(r) + \sigma_W c_W(r) \tag{4}$$

and accordingly for the permittivity $$\varepsilon_T(r) \approx \varepsilon_F c_F(r) + \varepsilon_W c_W(r) \tag{5}$$

since conductivity and permittivity can be approximated linearly. This rough map of electric properties might be used directly, where a rough estimation is sufficient (e.g., for hyperthermia treatment planning or SAR modelling). Alternatively, it can be used as starting point for iterative EPT algorithms as known per se from Lee J S et al., ISMRM 2013; 21:4183 and Balidemaj E et al., ISMRM 2013; 21:4185.

Execution of the machine-executable instructions further causes the processor to calculate at least one calculated electrical conductivity map using the zero echo time B1 phase map. This example may have the benefit that the electrical conductivity map can be determined at the same time that the n-point Dixon method is performed.

In another example execution of the machine-executable instructions further causes the processor to calculate a fat image and a water image when analyzing the magnetic resonance data according to the n-point Dixon method.

In another example execution of the instructions further causes the processor to identify fat regions within the subject by segmenting the fat image. Execution of the instructions further causes the processor to identify water regions within the subject by segmenting the water image. This segmentation could for instance be done in different ways. A model, such as a deformable-shaped body model or an anatomical atlas could be used to assist in the segmentation or a raw analysis of the voxels of the fat image and the water image could be used. For instance the fat image and the water image could be thresholded to produce the data about where the fat regions and the water regions are. In some examples the fat regions may include regions that are partially filled with water. Likewise the water regions may partially include fatty tissue.

In another example execution of the instructions further causes the processor to divide the subject into multiple differential kernel regions using the fat regions and the water regions. Execution of the instructions further causes the processor to determine boundary conditions between the multiple different kernel regions. The at least one calculated electrical conductivity map is calculated using the boundary conditions between the multiple differential kernel regions. This example may be particularly beneficial because the data from the fat and water images is used to produce boundary conditions which may improve the quality or accuracy of the calculation of the calculated electrical conductivity map. The fat and water regions may have different electrical properties. By explicitly making boundary conditions between these regions the at least one calculated electrical conductivity map can be calculated more accurately.

In another example the at least one calculated electrical conductivity map is calculated using a kernel that solves differential equations.

In another example execution of the instructions further causes the processor to calculate an estimated electrical conductivity map and an estimated permittivity map using the fat regions and the water regions. The estimated electrical conductivity map and the estimated permittivity map are only calculated using knowledge of the properties of fat and water. Calculating these two maps may be useful because they can be used to directly calculate other properties or may be used as starting conditions for solving the differential equations or for other numerical methods.

In another example the magnetic resonance imaging system further comprises an electromagnetic tissue heating system. An electromagnetic tissue heating system as used herein encompasses a system which is used to heat the tissue of a subject using electromagnetic radiation. Execution of the instructions further causes the processor to estimate spatially dependent heating of the subject using the estimated electrical conductivity map and the estimated permittivity map. Using the estimated electrical conductivity map and the estimated permittivity map to get the heating of the subject may be useful for treatment planning and also to avoid overheating portions of the subject.

In another example the spatially dependent heating of the subject is estimated using the at least one calculated electrical conductivity map and the estimated permittivity map. This may be beneficial because with knowledge of the zero echo time B1 phase map only the electrical conductivity can be calculated.

In another example the tissue heating system is a microwave tissue heating system.

In another example the tissue heating system is a radiofrequency tissue heating system.

In another example execution of the instructions further causes the processor to receive additional pulse sequence data. Execution of the instructions further causes the processor to model the specific absorption ratio of the subject for the additional pulse sequence data using the estimated electrical conductivity map or the at least one calculated electrical conductivity map and the estimated permittivity map. This may be beneficial because it may help predicting heating of the subject and avoiding injury of the subject.

In another example execution of the instructions further causes the processor to calculate the at least one electrical conductivity map using the zero echo time B1 map with an iterative solver. The iterative solver may be used to solve the solution for the at least one electrical conductivity map and an iterative method for solving the differential equations. The iterative solver is configured for using the estimated electrical conductivity map and the estimated permittivity map at least partially to determine an initial solution for initializing the iterative solver.

In another example execution of the instructions causes the processor to identify the fat regions by selecting regions with a fat-to-water ratio within a first predefined range. For example the first predefined range may define a threshold where voxels above a particular value are identified as being fat regions. In other examples the regions are within a particular range of values for the voxel.

In another example execution of the instructions further causes the processor to identify the water regions by selecting regions with a fat-to-water ratio within a second predefined range. As with the fat regions this could be done by thresholding or by plotting a fat-to-water ratio within a particular range of values. The values of the first predefined range are greater than the values of the second predefined range.

In another example the at least one electrical conductivity map comprises a water electrical conductivity map and a fat electrical conductivity map. Execution of the instructions causes the processor to calculate the water electrical conductivity map using the zero echo time B1 phase map for voxels in the water image with an intensity above a first predetermined threshold. Execution of the instructions further causes the processor to calculate the fat electrical conductivity map using the zero echo time B1 phase map for voxels in the water fat image with an intensity above a second predetermined threshold. In this example the two maps are calculated separately. This may have the effect of simplifying or stabilizing the calculation or solution of the differential equations.

In another example execution of the instructions further causes the processor to calculate a combined electrical conductivity map by combining the water electrical conductivity map and the fat electrical conductivity map. In this example the two images are combined to create a combined electrical conductivity map.

In another aspect an example provides for a method of operating the magnetic resonance imaging system for acquiring magnetic resonance data from a subject within an imaging zone. The method comprises the step of acquiring magnetic resonance data by controlling the magnetic resonance imaging system using the Dixon pulse sequence data. The Dixon pulse sequence data comprises instructions for controlling the magnetic resonance imaging system to acquire magnetic resonance data according to an n-point Dixon method. n is greater than or equal to 2. The method further comprises the step of estimating a B0 inhomogeneity map and estimating an estimated B1 phase map by analyzing the magnetic resonance data according to the n-point Dixon method. The method further comprises the step of calculating a zero echo time B1 phase map by interpolating the estimated B1 phase map to an echo time of zero using the B0 inhomogeneity map. The method further comprises the step of calculating at least one calculated electrical conductivity map using the zero echo time B1 phase map.

In another aspect an example provides for a computer program product comprising machine-executable instructions for execution by a processor controlling the magnetic resonance imaging system for acquiring magnetic resonance data from a subject within an imaging zone. Execution of the machine-executable instructions causes the processor to acquire magnetic resonance data by controlling the magnetic resonance imaging system using Dixon pulse sequence data. The Dixon pulse sequence data comprises instructions for controlling the magnetic resonance imaging system to acquire magnetic resonance data according to an n-point Dixon method. n is equal to or greater than 2.

Execution of the instructions further causes the processor to estimate a B0 inhomogeneity map and estimate an estimated B1 phase map by analyzing the magnetic resonance data according to the n-point Dixon method. Execution of the instructions further causes the processor to calculate a zero echo time B1 phase map by interpolating the estimated B1 phase map to an echo time of zero using the B0 inhomogeneity map. Execution of the machine-executable instructions further causes the processor to calculate at least one calculated electrical conductivity map using the zero echo time B1 phase map.

The presence of metallic objects may cause magnetic field inhomogeneities which lead to geometric distortions of the imaged voxels. This geometric distortion of the voxels may therefore lead to errors in values calculated with differential equations. For example, when performing electrical properties tomography the electrical conductivity and permittivity are calculated using differential equations. However, it is possible to correct for or account for the magnetic field inhomogeneities directly within the calculation of the derivatives.

In one aspect the invention provides for a magnetic resonance imaging system for acquiring magnetic resonance data from a subject within an imaging zone. The magnetic resonance imaging system comprises a memory for storing machine-executable instructions and pulse sequence data. The pulse sequence data comprises instructions for controlling the magnetic resonance imaging system to acquire magnetic resonance data according to a magnetic resonance imaging method. The magnetic resonance imaging system further comprises a processor for controlling the magnetic resonance imaging system.

Execution of the machine-executable instructions causes the processor to acquire the magnetic resonance data by controlling the magnetic resonance imaging system with the pulse sequence data. In some cases the pulse sequence data may comprise more than one pulse sequence. The magnetic resonance data may therefore be formed from more than one dataset. Execution of the machine-executable instructions further cause the processor to calculate a B0 inhomogeneity map by analyzing the magnetic resonance data according to the magnetic resonance imaging method. Execution of the instructions further cause the processor to calculate a B1 phase map and/or a B1 amplitude map by analyzing the magnetic resonance data according to the magnetic resonance imaging method.

Execution of the machine-executable instructions further cause the processor to calculate a second derivative of the B1 phase map and/or calculate a second derivative of the B1 magnitude map and/or calculate a second derivative of the B0 inhomogeneity map in at least one predetermined direction. The second derivative is calculated using a corrected voxel size in the at least one predetermined direction. The corrected voxel size is calculated using a correction factor calculated from the derivative of the B0 inhomogeneity map.

This embodiment may be beneficial because it may provide for a means of calculating the second derivative of the B1 phase map, the second derivative of the B1 magnitude map, or even the second derivative of the B0 inhomogeneity map more accurately.

In another embodiment execution of the machine-executable instructions further cause the processor to calculate a zero echo time B1 phase map by interpolating the B1 phase map to an echo time of zero using the B0 inhomogeneity map. The second derivative of the B1 phase map is calculated using a zero echo time B1 phase map.

In another embodiment the pulse sequence data is Dixon pulse sequence data. The magnetic resonance imaging method is an n-point Dixon method. n is greater than or equal to 2. The B0 inhomogeneity map and the B1 phase map are estimated by analyzing the magnetic resonance data according to the n-point Dixon method.

In another embodiment execution of the machine-executable instructions further cause the processor to calculate a fat image and a water image when analyzing the magnetic resonance data according to the n-point Dixon method. Execution of the machine-executable instructions further causes the processor to identify fat regions within the subject by segmenting the fat image. Execution of the machine-executable instructions further causes the processor to identify water regions within the subject by segmenting the water image. Execution of the machine-executable instructions further cause the processor to calculate an estimated electrical conductivity map and/or an estimated permittivity map using the fat regions and the water regions.

In another embodiment the magnetic resonance imaging system further comprises an electromagnetic tissue heating system. Execution of the instructions further cause the processor to estimate spatially dependent heating of the subject using the estimated permittivity map. Execution of the machine-executable instructions further cause the processor to further estimate the heating of the subject using the estimated electrical conductivity map and/or the at least one calculated electrical conductivity map.

In another embodiment the pulse sequence data comprises a multi-echo pulse sequence for measuring the B0 map. The pulse sequence data comprises B0 mapping pulse sequence data. In some examples the pulse sequence data further comprises a B1 magnitude measuring pulse sequence for measuring the B1 magnitude map. The pulse sequence data further comprises B1 magnitude mapping pulse sequence data. In a further example the pulse sequence data further comprises a B1 phase measuring pulse sequence for measuring the B1 phase map. The pulse sequence data comprises B1 phase mapping pulse sequence data. In yet a further example the pulse sequence data further comprises both a B1 magnitude measuring pulse sequence and the B1 phase measuring pulse sequence.

In this combined example both the B1 magnitude and B1 phase are measured that are acquired in separate scans of the magnetic resonance data.

In another embodiment the multi-echo pulse sequence comprises instructions for controlling the magnetic resonance imaging system to acquire magnetic resonance data according to any one of the following magnetic resonance imaging methods: an n-point Dixon method and a multi-echo pulse sequence method.

In another embodiment the B1 magnitude measuring pulse sequence comprises instructions for controlling the magnetic resonance imaging system to acquire magnetic resonance data according to any one of the following magnetic resonance imaging methods: an actual flip-angle imaging (AFI) magnetic resonance imaging method, a dual refocusing echo acquisition mode (DREAM) magnetic resonance imaging method, and a Bloch-Siegert shift magnetic resonance imaging method.

In another embodiment the B1 phase measuring pulse sequence comprises instructions for controlling the magnetic resonance imaging system to acquire magnetic resonance data according to any one of the following magnetic resonance imaging methods: a spin echo based magnetic resonance imaging method and a balanced gradient echo magnetic resonance imaging method.

In another embodiment execution of the machine-executable instructions further causes the processor to calculate the at least one calculated electrical conductivity map using the second derivative of the B1 phase map in the at least one predetermined direction.

In another embodiment execution of the machine-executable instructions further cause the processor to calculate at least one susceptibility map using the second derivative of the B0 inhomogeneity map in the at least one predetermined direction according to a quantitative susceptibility mapping method.

In another embodiment the pulse sequence data specifies a readout gradient for each of the at least one predetermined direction. The corrected voxel size in each of the at least one predetermined direction is $$dx_{true}(\vec{r}) = dx_{nominal}\left(1 + \frac{f'(\vec{r})}{\gamma G_R}\right).$$

In this equation, x is one of the at least one predetermined direction, $\vec{r}$ is a location of a voxel, $dx_{nominal}$ is an nominal voxel size in the one of the at least one predetermined direction, $f'(\vec{r})$ is a derivative of the B0 inhomogeneity map in the one of the at least one predetermined direction, $\gamma$ is the gyromagnetic ratio, and $G_R$ is the strength of the readout gradient in the one of the at least one predetermined direction.

In another embodiment the second derivative of the B1 phase map is $$\Phi''(\vec{r}) = \frac{\Phi(x - dx_{nominal}) - 2\Phi(x) + \Phi(x + dx_{nominal})}{dx_{true}(\vec{r})^2}.$$

In this equation, $\Phi$ is any one of the following: the B1 phase map, the B1 magnitude map, and the B0 inhomogeneity map.

It should be noted that although the B0 inhomogeneity map is used to calculate $dx_{true}(\vec{r})$ the calculation of the second derivate for the B0 inhomogeneity map using the above equation results in a more accurate value.

In another aspect the invention provides for a method of operating a magnetic resonance imaging system for acquiring magnetic resonance data from a subject within the imaging zone. The method comprises the step of acquiring the magnetic resonance data by controlling the magnetic resonance imaging system with pulse sequence data. The pulse sequence data comprises instructions for controlling the magnetic resonance imaging system to acquire magnetic resonance data according to a magnetic resonance imaging method. The method further comprises the step of calculating a B0 inhomogeneity map by analyzing the magnetic resonance data according to the magnetic resonance imaging method.

The method further comprises the step of calculating a B1 phase map and/or a B1 amplitude map by analyzing the magnetic resonance data according to the magnetic resonance imaging method. The method further comprises the step of calculating a second derivative of the B1 phase map and/or a second derivative of the B1 magnitude map and/or a second derivative of the B0 inhomogeneity map in the at least one predetermined direction. The second derivative is calculated using a corrected voxel size in the at least one predetermined direction. The corrected voxel size is calculated using a correction factor calculated from the derivative of the B0 inhomogeneity map in the at least one predetermined direction.

In another aspect the invention provides for a computer program product comprising machine-executable instructions for execution by a processor controlling a magnetic resonance imaging system for acquiring magnetic resonance data from a subject within an imaging zone. Execution of the machine-executable instructions causes the processor to acquire the magnetic resonance data by controlling the magnetic resonance imaging system with the pulse sequence data. The pulse sequence data comprises instructions for controlling the magnetic resonance imaging system to acquire magnetic resonance data according to a magnetic resonance imaging method. Execution of the machine-executable instructions further cause the processor to calculate a B0 inhomogeneity map by analyzing the magnetic resonance data according to the magnetic resonance imaging method.

Execution of the machine-executable instructions further cause the processor to calculate a B1 phase map and/or a B1 amplitude map by analyzing the magnetic resonance data according to the magnetic resonance imaging method. Execution of the machine-executable instructions further cause the processor to calculate a second derivative of the B1 phase map and/or a second derivative of the B1 magnitude map and/or second derivative of the B0 inhomogeneity map in the at least one predetermined direction. The second derivative is calculated using the corrected voxel size in the at least one predetermined direction. The corrected voxel size is calculated using a correction factor calculated from the derivative of the B0 inhomogeneity map.

It is understood that one or more of the aforementioned embodiments of the invention and/or examples may be combined as long as the combined embodiments and/or examples are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
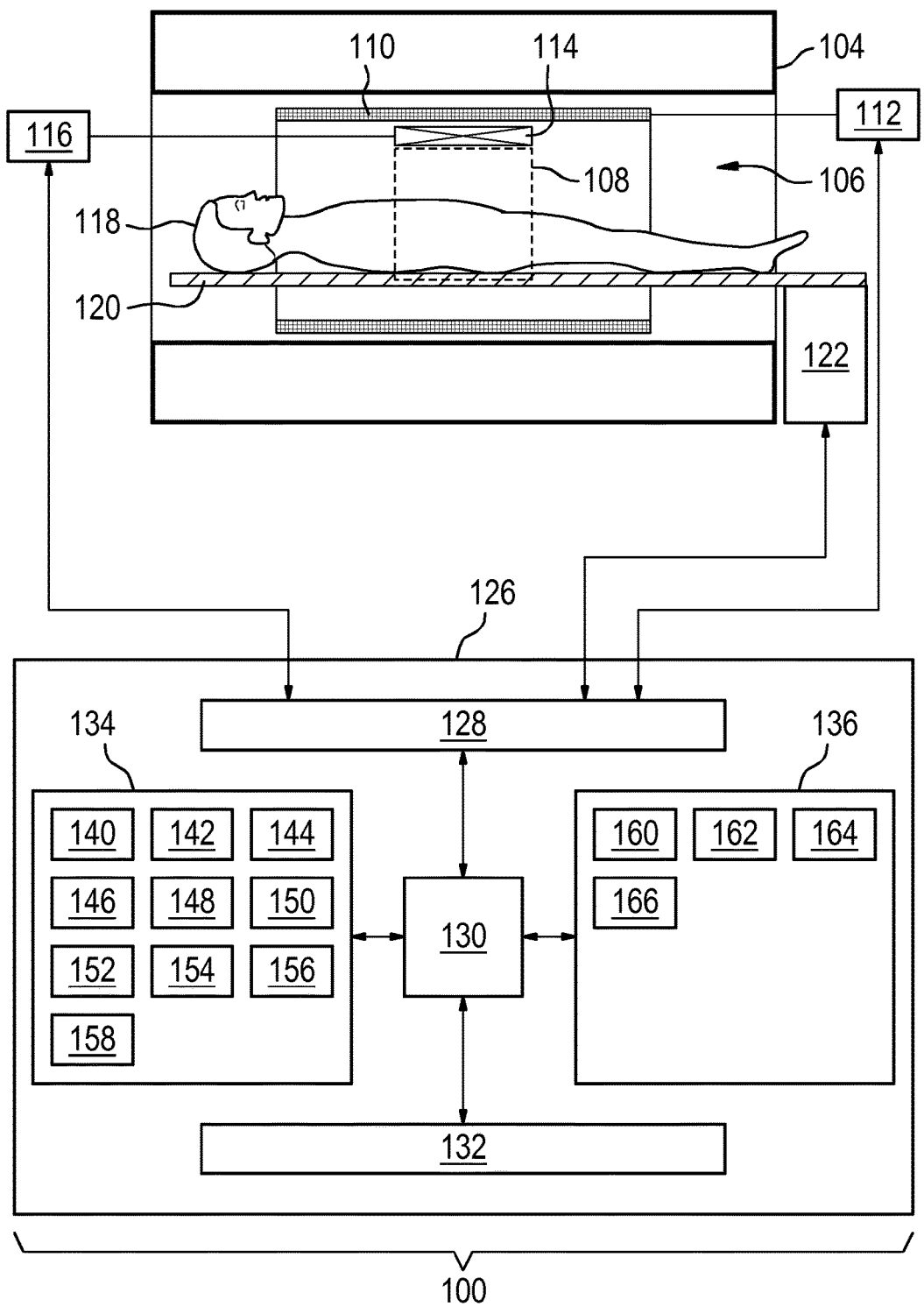
FIG. 1 illustrates an example of a magnetic resonance imaging system.

FIG. 1 shows an example of a magnetic resonance imaging system 100 with a magnet 104. The magnet 104 is a superconducting cylindrical type magnet 104 with a bore 106 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet, there is a collection of superconducting coils. Within the bore 106 of the cylindrical magnet 104 there is an imaging zone 108 where the magnetic field is strong and uniform enough to perform magnetic resonance imaging.

Within the bore 106 of the magnet there is also a set of magnetic field gradient coils 110 which is used for acquisition of magnetic resonance data to spatially encode magnetic spins within the imaging zone 108 of the magnet 104. The magnetic field gradient coils 110 are connected to a magnetic field gradient coil power supply 112. The magnetic field gradient coils 110 are intended to be representative. Typically magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

Adjacent to the imaging zone 108 is a radio-frequency coil 114 for manipulating the orientation of magnetic spins within the imaging zone 108 and for receiving radio transmissions from spins also within the imaging zone 108. The radio frequency antenna may contain multiple coil elements. The radio frequency antenna may also be referred to as a channel or antenna. The radio-frequency coil 114 is connected to a radio frequency transceiver 116. The radio-frequency coil 114 and radio frequency transceiver 116 may be replaced by separate transmit and receive coils and a separate transmitter and receiver. It is understood that the radio-frequency coil 114 and the radio frequency transceiver 116 are representative. The radio-frequency coil 114 is intended to also represent a dedicated transmit antenna and a dedicated receive antenna. Likewise the transceiver 116 may also represent a separate transmitter and receiver. The radio-frequency coil 114 may also have multiple receive/transmit elements and the radio frequency transceiver 116 may have multiple receive/transmit channels.

Within the bore 106 of the magnet 104 there is a subject support 120 which is attached to an optional actuator 122 that is able to move the subject support and the subject 118 through the imaging zone 108. The transceiver 116, the magnetic field gradient coil power supply 112 and the actuator 122 are all seen as being connected to a hardware interface 128 of computer system 126.

The contents of the computer storage 134 and the computer memory 136 may be interchangeable. In some examples the contents of the computer storage 134 may be duplicated in the computer memory 136.

The computer storage 134 is shown as containing the Dixon pulse sequence data. The computer storage 134 is further shown as containing magnetic resonance data 142 that has been acquired by controlling the magnetic resonance imaging system 100 with the Dixon pulse sequence data 140. The computer storage 134 is further shown as containing a fat image 144 and a water image 146 that have been reconstructed from the magnetic resonance data 142 according to the Dixon method. The computer storage 134 is further shown as containing a B0 inhomogeneity map 148 and an estimated B1 phase map 150 that have also been calculated using the Dixon method. The computer storage 134 is further shown as containing a zero echo time B1 phase map 152 that has been calculated by interpolating the estimated B1 phase map to an echo time of 0 using the B0 inhomogeneity map. The computer storage 134 is further shown as containing electrical conductivity maps 154 that have been calculated using the zero echo time B1 phase map. The computer storage 134 is further shown as containing fat region location data 156 and the water region location data 158 that have been determined from the fat image 144 and the water image 146 respectively. These may even be determined for instance by performing image processing on the fat image 144 and the water image 146.

The computer memory 136 is shown as containing a control module 160. The control module 160 contains computer executable code which enables the processor 130 to control the magnetic resonance imaging system 100. For instance the control module 160 may enable the processor 130 to control the magnetic resonance imaging system 100 with the Dixon pulse sequence data 140 to acquire the magnetic resonance data 142. The computer memory 136 is further shown as containing an image reconstruction module 162. The image reconstruction module 162 enables the processor 130 to process the magnetic resonance data 142 into the fat image 144, the water image 146, the B0 inhomogeneity map 148, and the estimated B1 phase map 150. The image reconstruction module essentially enables the processor 130 to perform the data analysis aspects of the Dixon method.

The computer memory 136 is further shown as containing an image processing module 164. The image processing module 164 enables the processor 130 to perform various image processing tasks on image data. For instance the fat region location data 156 and the water region location data 158 could be determined from the fat image 144 and the water image 146. The computer memory 136 is further shown as containing a differential equation kernel module 166. The differential equation kernel module 166 contains a differential equation solver which enables the processor 130 to calculate the one or more electrical conductivity maps 154 according to the various methods described herein.

Figure 2:
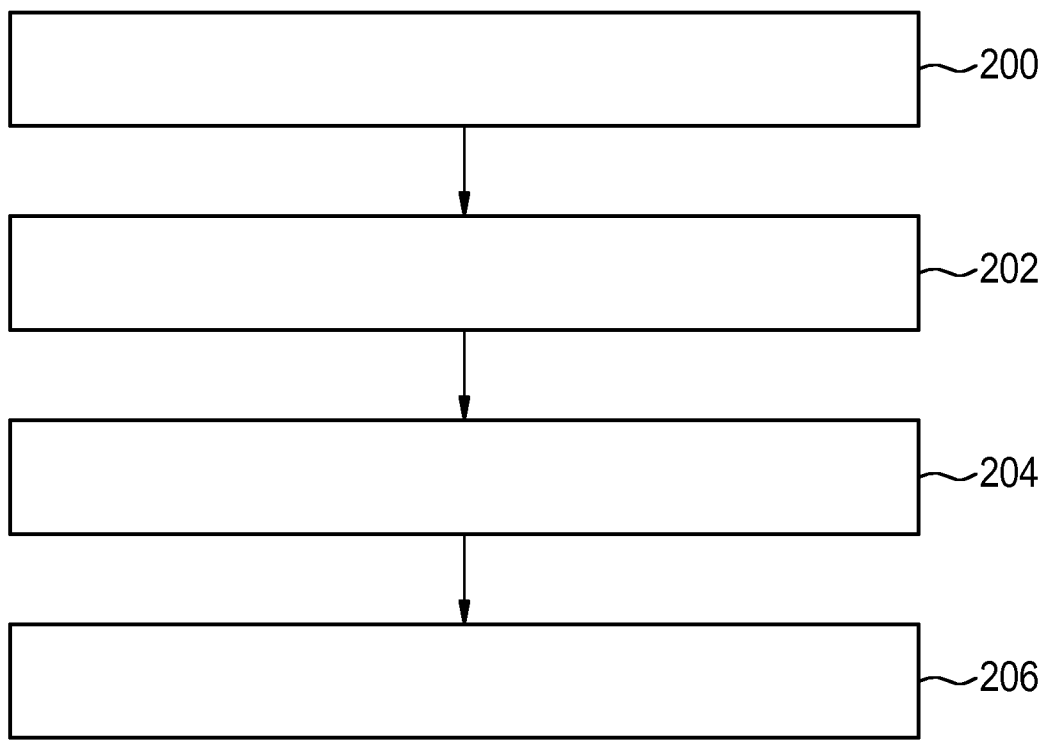
FIG. 2 shows a flow chart of a method of operating the magnetic resonance imaging system of claim 1.

FIG. 2 shows a flowchart which illustrates a method of operating the magnetic resonance imaging system 100 of FIG. 1. First in step 200 the magnetic resonance data 142 is acquired by controlling the magnetic resonance imaging system with the Dixon pulse sequence data 140. Next in step 202 the B0 inhomogeneity map 148 and the estimated B1 phase map 150 are calculated by analyzing the magnetic resonance data according to an n-point Dixon method. Next in step 204 a zero echo time B1 phase map 152 is calculated by interpolating the estimated B1 phase map 150 to an echo time of 0 using the B0 inhomogeneity map 148. Finally in step 206, the at least one electrical conductivity map 154 is calculated using the zero echo time B1 phase map 152.

Figure 3:
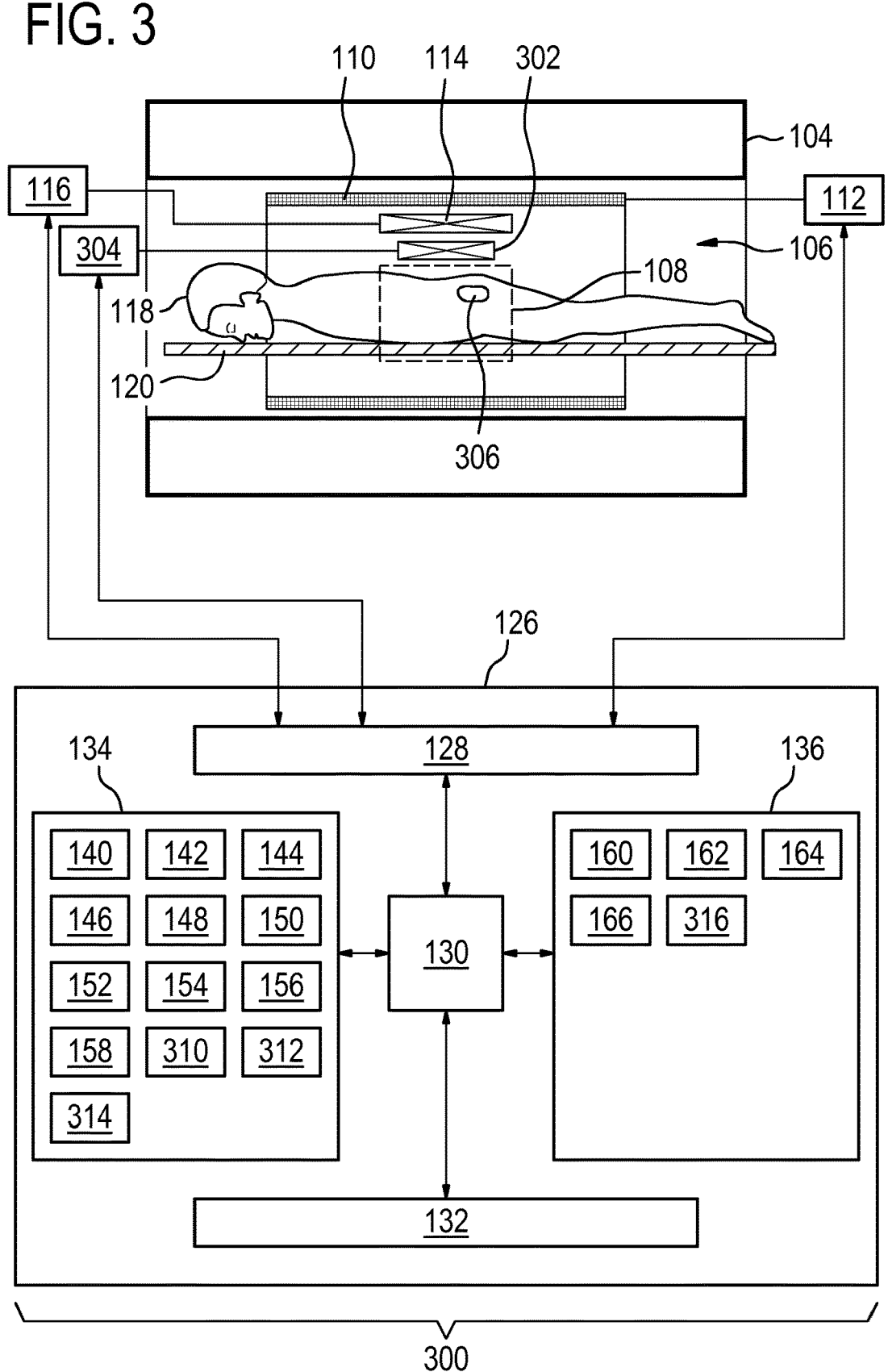
FIG. 3 illustrates a further example of a magnetic resonance imaging system.

FIG. 3 shows a further example of a magnetic resonance imaging system 300. In this example the magnetic resonance imaging system 300 also includes a tissue heating system formed by an antenna 302 adjacent to the subject 118 and by a radio-frequency transmitter 304. The combination of the antenna 302 and the radio-frequency transmitter 304 are exemplary. For example this could be replaced with a system that generates microwave or other electromagnetic radiation for heating the subject 118. The subject 118 is shown as having a target zone 306 that is desired to be heated within the subject 118.

The computer storage 134 is shown as containing a treatment plan 312. The treatment plan 312 may be descriptive of the internal structure of the subject 118 and contain data which enables identification or location of the target zone 306. Computer storage 134 further contains a set of heating system control commands 314 that have been generated using the treatment plan 312. The heating system control commands 314 contain commands which enable the processor 130 to control the operation and function of the heating system 302, 304. The computer memory 136 is further shown as containing a heating system control generation module 316. The heating system control generation module 316 contains computer executable code which enables the processor 130 to generate the heating system control commands 314 from the treatment plan 312 and possibly from magnetic resonance data acquired by the magnetic resonance imaging system 300.

The radio-frequency heating system comprises an antenna 302 and a radio-frequency transmitter 304. The antenna 302 is in the vicinity of target zone 306. Radio-frequency energy generated by the transmitter 304 and radiated by the antenna 302 is used to selectively heat the target zone 306. In this embodiment the radio-frequency transmitter 304 is shown as being connected to the hardware interface 128.

The computer storage 134 is shown as having an estimated permittivity map 310 that was calculated by knowing the permittivity properties of fat and water and then using the fat region location data 156 and the water region location data 158 to calculate the estimated electrical permittivity.

The heating system control generation module 316 can use the estimated permittivity map 310 and the at least one electrical conductivity map 154 to estimate heating of the subject 118 by the antenna 302. This may enable a more accurate calculation or determination of the heating system control commands 314.

Examples describe herein may combine Electric Properties Tomography (EPT) with Dixon scanning EPT can benefit from prior knowledge like the water/fat tissue composition to ease and to make the reconstruction more robust. Three possible major synergy effects have been identified:

Reduced scan time by simultaneous EPT and water/fat imaging. This might expand the scope of sequences EPT is applicable to.

Improved conductivity estimation using the fat/water image information as starting point for iterative EPT.

An optimization of the image segmentation process required in the EPT reconstruction by segmenting fat/water images instead of standard (T1/T2 weighted) images.

Electric tissue properties (conductivity and permittivity) can be determined in vivo by applying the Helmholtz equation to the RF transmit (and/or receive) field. Basically, EPT requires the "direct" solution of an inverse problem. However, advanced studies show advantages of solving the forward problem iteratively, starting with a suitable initial guess of electric properties.

In general the human body consists roughly of 65% water, 10% fat (sometimes more) and 20% proteins and minerals, where the latter two are often difficult to detect directly by proton MR. Water-rich tissue has obviously a significantly higher conductivity than fat, which is often seen as a kind of electrical isolator. Fat and water contributions to the received MR signal can be separated based on a chemical shift encoded acquisition using so-called Dixon methods. The chemical shift encoding is usually achieved by repeated measurements at different echo times, and the fat-water separation commonly involves an estimation of the underlying main field (B0) inhomogeneity.

EPT is hampered by a couple of physical/technical drawbacks. For this invention, three of these drawbacks are considered.

EPT requires phase data purely related to RF penetration (i.e., free of contributions from B0 inhomogeneities), which usually is fulfilled sufficiently only for spin-echo based sequences. Thus, if a patient exam contains only field-echo based sequences, EPT requires additional scan time using dedicated MRI sequences.

Iterative EPT reconstruction algorithms require a suitable starting point. This is typically realized by applying standard EPT (solving the inverse problem) or by applying literature values of the electric properties to the compartments of the individual patient. Both methods are time-consuming.

The numerical differentiation kernel required for EPT should not contain voxels from different compartments, requiring suitable image segmentation. Image segmentation is sometimes hampered by low contrast between tissue compartments.

Examples may have one or more of the following features;

The required RF phase purely related to RF penetration can be extracted from a Dixon scan without further scans. Furthermore, the obtained B0 map can be used to apply EPT also to other field-echo based sequences.

Since (pure) fat and (pure) water have typical (fixed, known) electric properties values, the total (superposed fat/water) electric properties can be roughly estimated by the fat/water ratio given by the Dixon scan. This rough map of electric properties might be used directly (e.g., for SAR modelling), or as starting point for iterative EPT algorithms.

For some compartments, water and fat images show higher contrast than anatomic images, yielding a more reliable segmentation of the compartments investigated.

The basic equation for EPT is:

$$\frac{-\nabla^2 B_1}{\mu_0 \omega B_1} = \omega\varepsilon - i\sigma \qquad (1)$$

with $\varepsilon$ the permittivity, $\sigma$ the electric conductivity, $\mu_0$ the vacuum permeability, and $\omega$ the Larmor frequency of the MR system applied. Frequently, a constant $B_1$ amplitude can be assumed, reducing Eq. (1) to conductivity imaging based only on the $B_1$ phase $\varphi$ $$\frac{\nabla^2 \varphi}{\mu_0 \omega} = \sigma. \quad (2)$$

The basic equation for Dixon methods is given by $$S_n = (W + Fe^{i\vartheta_n})e^{i\varphi_n} \quad (3)$$

with $S_n$ the measured composite signal at echo time $TE_n$, $W$ the unknown water signal, $F$ the unknown fat signal, $\vartheta_n$ the known phase offset between fat and water signal at $TE_n$, induced by the difference in chemical shift between fat and water, and $\varphi_n$ the unknown phase error at $TE_n$, typically induced primarily by $B_0$ inhomogeneities.

In the following, three different synergy effects of combing Dixon with EPT are discussed.

Combined Scanning

To skip a separate spin-echo scan for EPT phase determination, the phase evolution of the Dixon scans is extrapolated/demodulated to TE=0. At TE=0, the phase map is not affected by $B_0$ inhomogeneities, i.e., it represents the purely RF-related phase as required by EPT. It is assumed that no delay in the acquisition chain is present, which might result into a linear phase change in the spatial domain. However, using appropriate system tuning, this problem can be mitigated. In this way, Dixon data can be re-used for conductivity calculation without requiring additional scan time.

Electric Properties Estimation

Fatty tissue has a relative permittivity of around $\varepsilon_F = 10$ and a conductivity of around $\sigma_F = 0.05$ S/m. Blood (representing water) has a relative permittivity around $\varepsilon_W = 70$ and a conductivity around $\sigma_W = 1$ S/m. From the Dixon scan, relative concentrations of fat $c_F(r)$ and water $c_W(r)$ are obtained. In some of the Dixon applications some care is necessary to make these numbers really quantitative (see fat fraction quantification), because the signal intensity might be colored by the sequence parameters used. This yields an estimation of the total conductivity $\sigma_T(r)$ via $$\sigma_T(r) \approx \sigma_F c_F(r) + \sigma_W c_W(r) \quad (4)$$

and accordingly for the permittivity $$\varepsilon_T(r) \approx \varepsilon_F c_F(r) + \varepsilon_W c_W(r) \quad (5)$$

since conductivity and permittivity can be approximated linearly. This rough map of electric properties might be used directly, where a rough estimation is sufficient (e.g., for hyperthermia treatment planning or SAR modelling). Alternatively, it can be used as starting point for iterative EPT algorithms.

Image Segmentation

Image segmentation is required for EPT to ensure that numerical differentiation kernels do not cross boundaries of tissue compartments with different electric properties. This case is not covered by Eqs. (1,2) and would lead to strong oscillatory artefacts in the reconstructed electric properties along the compartment boundaries.

Image segmentation is typically based on differences in the magnitude of the MR signal between the compartments to be segmented. However, this difference is not always guaranteed, since electric properties have no direct impact on the MR signal magnitude. Fat and water images can support image segmentation, since they provide a different contrast than standard (composite) MR images. It is also possible to base segmentation on multiple images, combining areas of locally highest contrast from different images.

Alternatively, image segmentation can be taken into account by applying two separate EPT reconstructions: the first reconstruction based on the water image, the second reconstruction based on the fat image. The resulting two conductivity maps can be separately used for diagnostics, or combined using Eqs (4,5) replacing the mean values by the reconstructed spatial distributions with $\varepsilon_F = \varepsilon_F(r)$, $\sigma_F = \sigma_F(r)$, $\varepsilon_W = \varepsilon_W(r)$, $\sigma_W = \sigma_W(r)$. This procedure has the additional advantage that potential chemical shift artefacts do not deteriorate the EPT reconstruction.

Experimental Illustration

Figure 4:
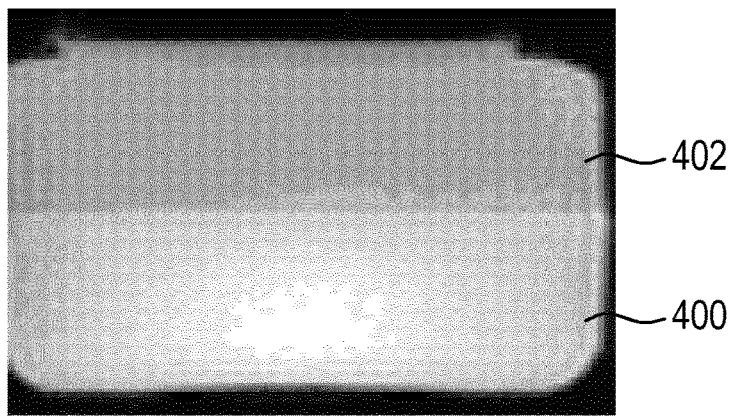
FIG. 4 shows the magnitude image from an mDixon image.

In the following, the three different synergy effects claimed for combing Dixon with EPT are illustrated by a phantom experiment. The phantom is a bottle with saline (in the lower part of bottle) and oil (in the upper part of bottle). The magnitude image of echo 1 is shown in FIG. 4, the water image in FIG. 5, and the fat image in FIG. 6.

Combined Scanning

Mean conductivities obtained from the Dixon-based reconstruction are shown in Tab. 1. Additionally, a bFFE-based conductivity image (known to have spin-echo like properties) was acquired for comparison. The mean values of fat and water conductivity of the two approaches are very similar (see Tab. 1).

TABLE 1

Mean values of fat and water conductivity are very similar for Dixon-based conductivity and bFFE-based conductivity (known to have spin-echo like properties). This underlines the possibility of applying Dixon and EPT simultaneously. The third line demonstrates the possibility to roughly estimate the conductivity from the measured fat fraction.

|  | Water | fat |
|---|---|---|
| bFFE (reconstructed) | 0.73 ± 0.09 S/m | 0.01 ± 0.16 S/m |
| Dixon (reconstructed) | 0.76 ± 0.25 S/m | 0.01 ± 0.40 S/m |
| Dixon (estimated) | 0.99 S/m | 0.09 S/m |

Electric Properties Estimation

The Dixon scan yielded relative concentrations of $c_F = 1.3\%$ and $c_W = 98.7\%$ averaged over the saline compartment and $c_F = 95.4\%$ and $c_W = 4.6\%$ averaged over the oil compartment. According to Eq. (4), we can estimate the conductivity values as given in Tab. 1, reflecting roughly the explicitly reconstructed conductivity using Eq. (2).

Image Segmentation

Figure 5:
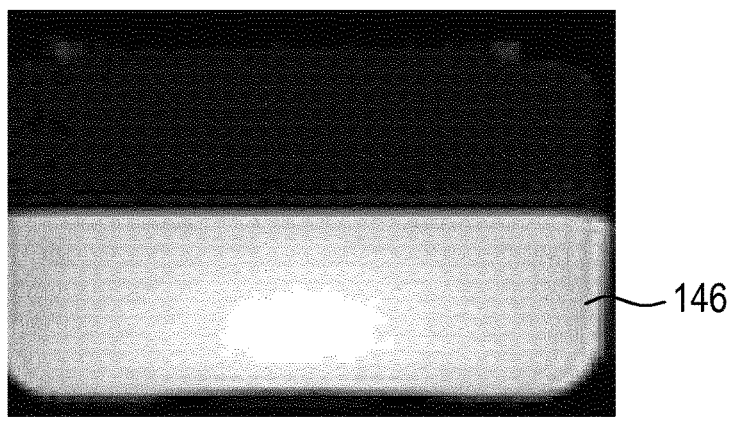
FIG. 5 shows the water separated image of the mDixon image of FIG. 4.
Figure 6:
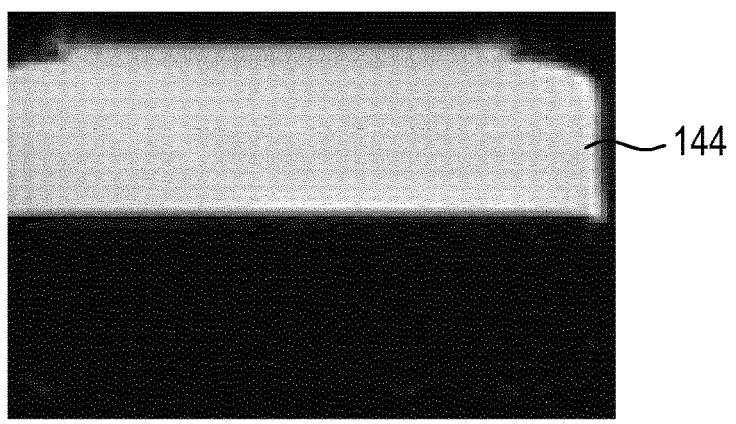
FIG. 6 shows the fat separated image of the mDixon image of FIG. 4.
Figure 7:
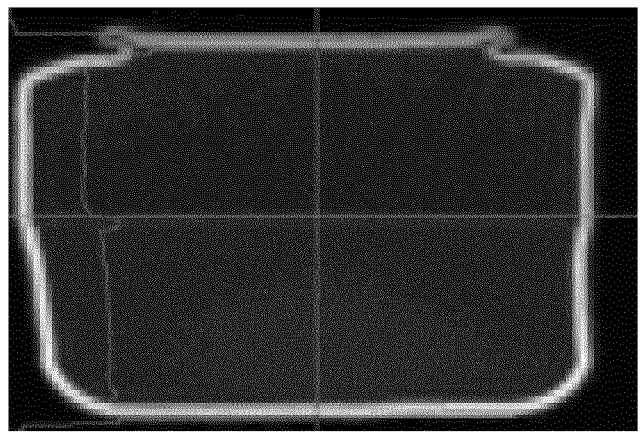
FIG. 7 shows a segmentation of FIG. 4 using a Laplace operator.
Figure 8:
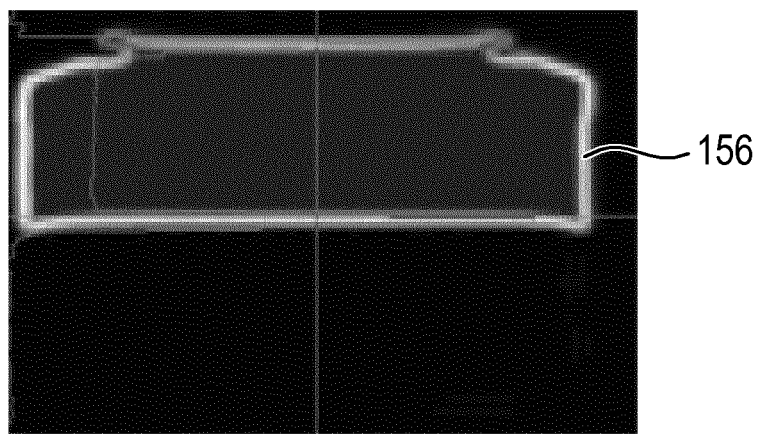
FIG. 8 shows a segmentation of FIG. 6 using a Laplace operator.
Figure 9:
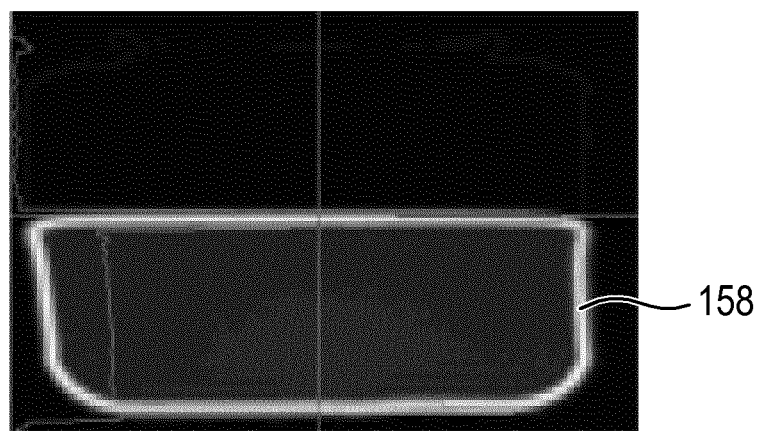
FIG. 9 shows a segmentation of FIG. 5 using a Laplace operator.

The three images shown in FIGS. 4 through 6 are segmented by means of a Laplace operator with the results shown in FIGS. 7 through 9. The oil/saline boundary is clearly better depicted by segmenting the fat (FIG. 6) or water image (FIG. 5) than the image of echo 1 (FIG. 4). The optimum segmentation is obtained by combing segmentations from the different images (FIG. 10, here combined by a maximum intensity projection). FIGS. 4, 5 and 6 show results from performing a two-point Dixon method on a phantom. The phantom has an upper part made of a fat-like phantom labeled 402 in FIG. 4 and a lower saline portion labeled 400 in FIG. 4. FIG. 4 shows the magnitude image from an mDixon image. FIG. 5 shows the water separated image 146. FIG. 6 shows the corresponding fat image 144.

FIG. 7 shows a segmentation of FIG. 4 using a Laplace operator. It can be seen in FIG. 7 that a clear delineation of the fat 402 and saline 400 regions is not shown in FIG. 7.

FIG. 8 shows a segmentation of FIG. 6 using the Laplace operator. As 6 is a fat image the segmentation in FIG. 8 indicates a fat region 156.

FIG. 9 shows a segmentation of FIG. 5 using the Laplace operator. As FIG. 5 is a water image 146 the segmentation in FIG. 9 indicates a water region 158.

Figure 10:
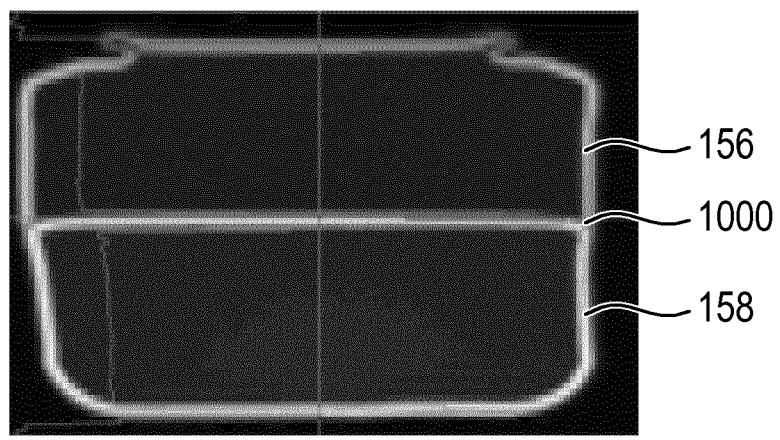
FIG. 10 shows a combination of images 8 and 9.

FIG. 10 shows a combination of FIGS. 8 and 9. The combination of FIGS. 8 and 9 shows a region which is identified as a fat region 156 and a water region 158. There is also a boundary region 1000 which is clearly identified between the two. This is much less pronounced in FIG. 7. FIG. 10 illustrates that the segmentation of images from a Dixon method can be used to identify fat and water regions within an image. This will be particularly useful in solving the differential equations for determining the electrical conductivity. Additionally the boundary region 1000 can be fed to the differential equation solver or kernel so that the appropriate boundary conditions between the fat region 156 and the water region 158 can be used.

Figure 11:
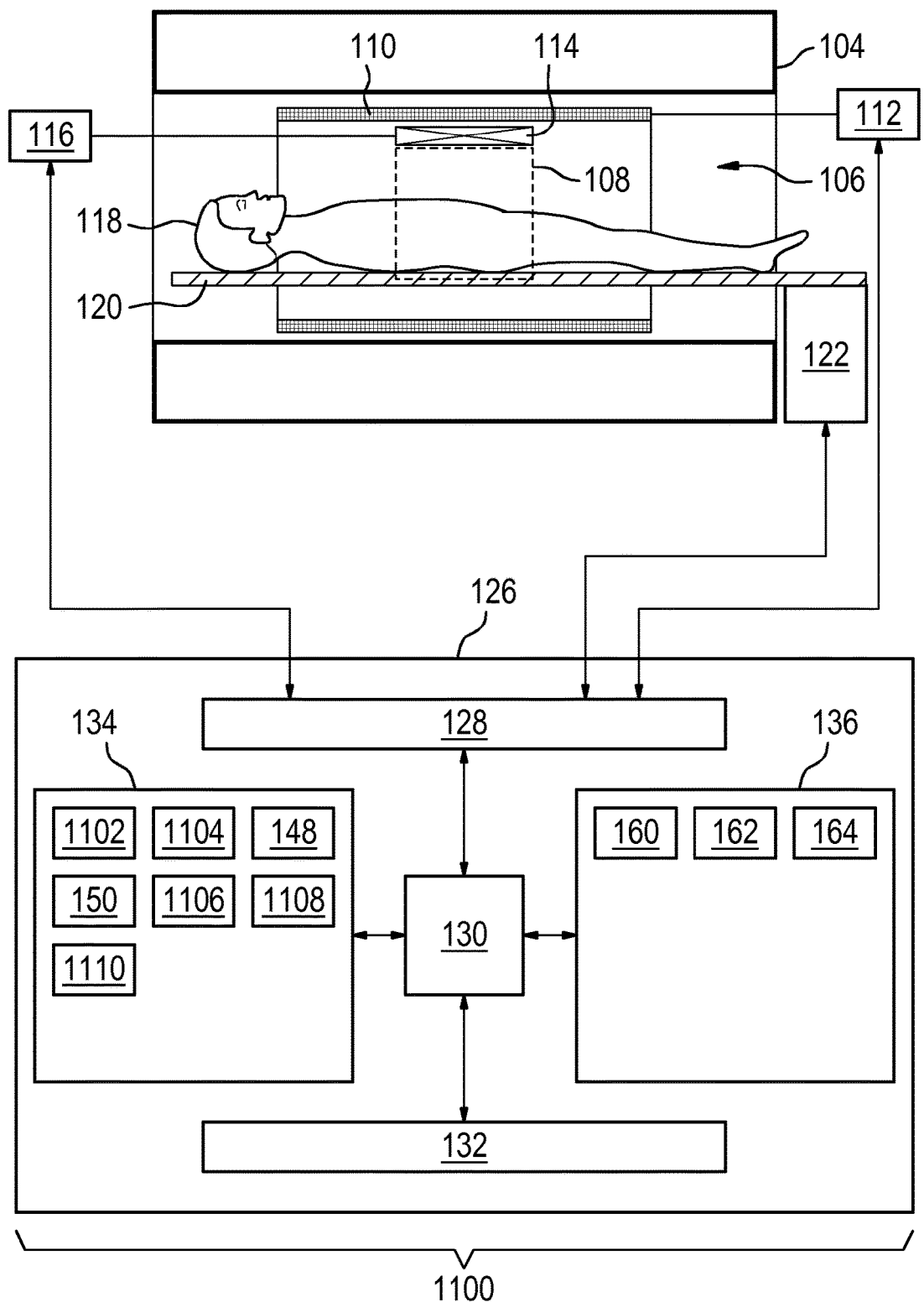
FIG. 11 shows a further example of a magnetic resonance imaging system.

FIG. 11 shows an example of a magnetic resonance imaging system 1100 that is similar to that shown in FIG. 1 and FIG. 3. The magnetic resonance imaging systems shown in FIGS. 1, 3 and 11 may have their features combined.

The computer storage 134 is shown as containing a pulse sequence data 1102 for controlling the magnetic resonance imaging system 1100. In some instances the pulse sequence data 1102 may be identical with the pulse sequence data 140 of FIG. 1. The computer storage 134 is further shown as containing magnetic resonance data 1104. In some cases the magnetic resonance data 1104 may be identical with the magnetic resonance data 142 of FIG. 1. The computer storage 134 is further shown as containing a B0 inhomogeneity map 148 that was determined using the magnetic resonance data 1104. The computer storage 134 is further shown as containing an estimated B1 phase map 150 and a B1 amplitude map 1106. Both the B1 phase map 150 and the B1 amplitude map 1106 are also calculated or derived from the magnetic resonance data 1104. The estimated B1 phase map 150 and the B1 amplitude map 1106 may not be present in all embodiments.

The computer memory 136 is shown as containing a control module 160, an image reconstruction module 162, and an image processing module 164. These modules are as described in FIG. 1 and/or FIG. 3. The image processing module 164 for instance may be used to calculate the correction factor for calculating the second derivative and also calculating the value of the second derivatives. The computer storage 134 is further shown as containing a corrected voxel size 1108 and a second derivative 1110. The second derivative may be representative of a B0 inhomogeneity map second derivative, a B1 phase map second derivative and/or a B1 amplitude map second derivative. The corrected voxel size 1108 and the second derivative 1110 may be calculated by numerical code which may be a separate module or may for instance be part of an image processing module 164.

Although this is not illustrated in FIG. 11 the computer storage 134 or computer memory 136 may contain additional data and/or numerical algorithms for performing such things as quantitative susceptibility mapping or electric properties tomography.

Figure 12:
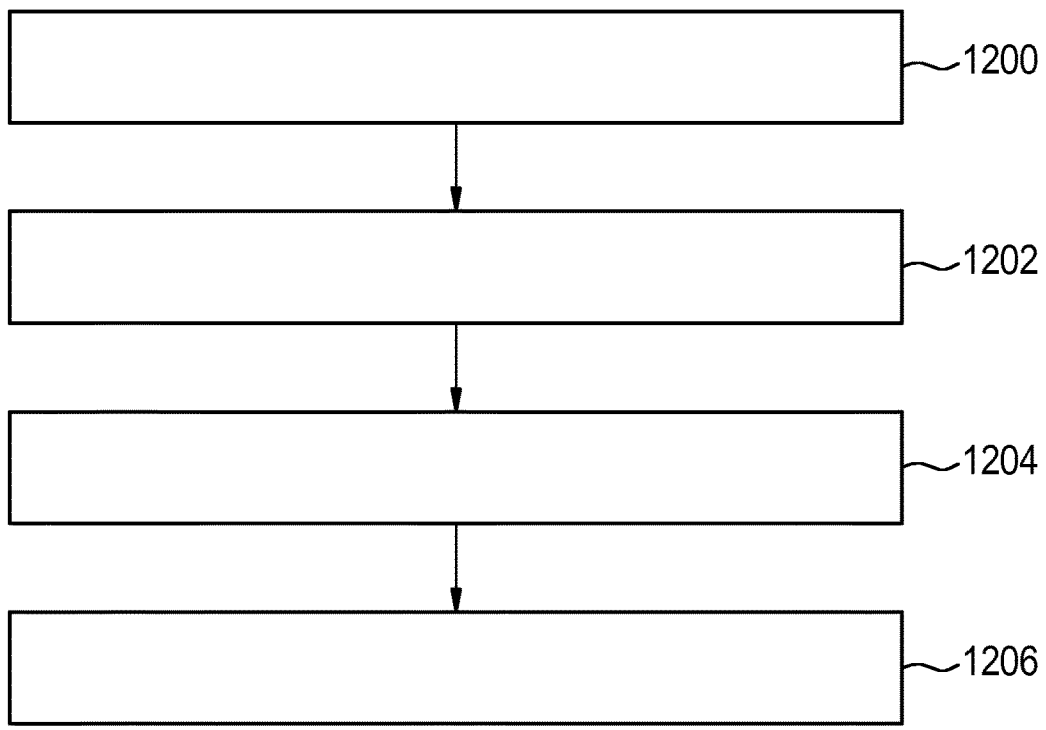
FIG. 12 shows a flow chart of a method of operating the magnetic resonance imaging system of claim 11.

FIG. 12 shows a flowchart which illustrates an example of a method of operating the magnetic resonance system 1100 of FIG. 11. First in step 1200 the magnetic resonance data 1104 is acquired by controlling the magnetic resonance imaging system 1100 with the pulse sequence data 1102. Next in step 1102 a B0 inhomogeneity map 148 is calculated by analyzing the magnetic resonance data 1104 according to a magnetic resonance imaging method. Next in step 1204 a B1 phase map 150 and/or a B1 amplitude map 1106 is calculated by analyzing the magnetic resonance data 142 according to the magnetic resonance imaging method. Finally in step 1206 a second derivative 1110 of the B1 phase map 150 and/or a second derivative of the B1 magnitude map 1106 and/or a second derivative of the B0 inhomogeneity map 148 is calculated in at least one predetermined direction. The second derivative is calculated using the corrected voxel size 1108 in the at least one predetermined direction. The corrected voxel size is calculated using a correction factor calculated from the derivative of the B0 inhomogeneity map 148.

Geometric distortions due to static inhomogeneities of the magnetic field adversely affect any image processing procedure which relies on spatial derivatives, e.g. Quantitative Susceptibility Mapping (QSM) or Electric Properties Tomography (EPT). In this invention, it is proposed to include the correction for the geometric distortion into the calculation of the derivatives instead. It is shown in a phantom experiment that the relative errors for second-order derivatives range between ±4% and can easily reach 50% under more adverse conditions.

Magnetic field distortions caused by the object placed in the MR scanner lead to additional, spatially varying magnetic field gradients. These additional gradients lead to geometric distortions of the reconstructed images in which the targeted nominal voxel size (as shown in scanner GUI) is different from the true (physical) voxel size. The distortions of the magnetic field can be measured by acquiring a B0-map (i.e., off-resonance map) using a suitable MR sequence.

Many emerging quantitative MR contrasts, for example Quantitative Susceptibility Mapping (QSM) or Electric Properties Tomography (EPT), rely on a physical model expressed as a differential equation. In order to extract a (bio-)physical tissue quantity, such as electric conductivity or magnetic susceptibility, derivatives of a suitable MR image are calculated using finite differences into which the voxel sizes enters. It is therefore important that the geometric distortions are taken into account to avoid systematic errors, which can exceed 50%.

Instead of differentiating geometrically corrected MR images, which might introduce artefacts, e.g. due to an interpolation step applied to the images, it is proposed here to correct the calculation of the derivatives themselves. This allows one to obtain quantitatively correct results in a single step and without further assumptions.

Given the off-resonance field map and the strength of the readout gradient $G_R$, a correction factor can be calculated for each spatial position relating the nominal voxel size to the true voxel size (in readout direction determined solely by $G_R$). The true voxel size at a given location in space, $dx_{true}(\vec{r})$, is given by:

$$dx_{true}(\vec{r}) = dx_{nominal}\left(1 + \frac{f'(\vec{r})}{\gamma G_R}\right)$$

Here f' is the derivative of the B0-map in readout direction and γ is the gyromagnetic ratio. Given an MR phase image, for example, its second derivative (important for e.g. phase-based EPT) in readout direction would then be calculated as:

$$\Phi''(\vec{r}) = \frac{\Phi(x - dx_{nominal}) - 2\Phi(x) + \Phi(x + dx_{nominal})}{dx_{true}(\vec{r})^2}$$

For not too large gradients of the field map, both the error in the voxel size and the order of the derivative enter linearly into the result. The higher the order of the derivative, the larger the error.

Experiments on a phantom (cylindrical basin filled with about 21 CuSO4 solution and several long balloons with varying concentrations of Resovist and Gadovist) were performed on a 3T magnetic resonance scanner with a 15-channel coil using a multi-echo gradient-echo sequence (FOV: (AP, FH, RL) 240×145×210 mm$^3$, acq voxel: 0.6× 0.6×2.0 mm$^3$, FA=14°, TE=3.5 ms, ΔTE=4 ms, 7 echoes, TR=31 ms, bipolar readout, BW=275.9 Hz/vx, SENSE (P/S) 1.8×1.2). Images for all echoes were reconstructed on the scanner and exported for further processing. The phase images from even echoes were used to calculate the B0-map assuming that the phase evolves linearly in time as a function of the off-resonance frequency f. The phase offset $\Phi_0$ is the phase offset at t=0:

$$\Phi(t) = \Phi_0 + 2\pi ft.$$

Phase images and field map were unwrapped using a best-path region-growing algorithm. To assess the effect of geometric distortion, the second derivative of the third even echo (ΔTE=19.4 ms) was calculated along the readout direction as described above. In the presented example, the resulting error ranges between ±4%, and can easily reach more than 50% under more adverse conditions, e.g. using echo-planar imaging or calculating higher-order derivatives. These experiments are summarized in FIGS. 13 and 14.

Figure 13:
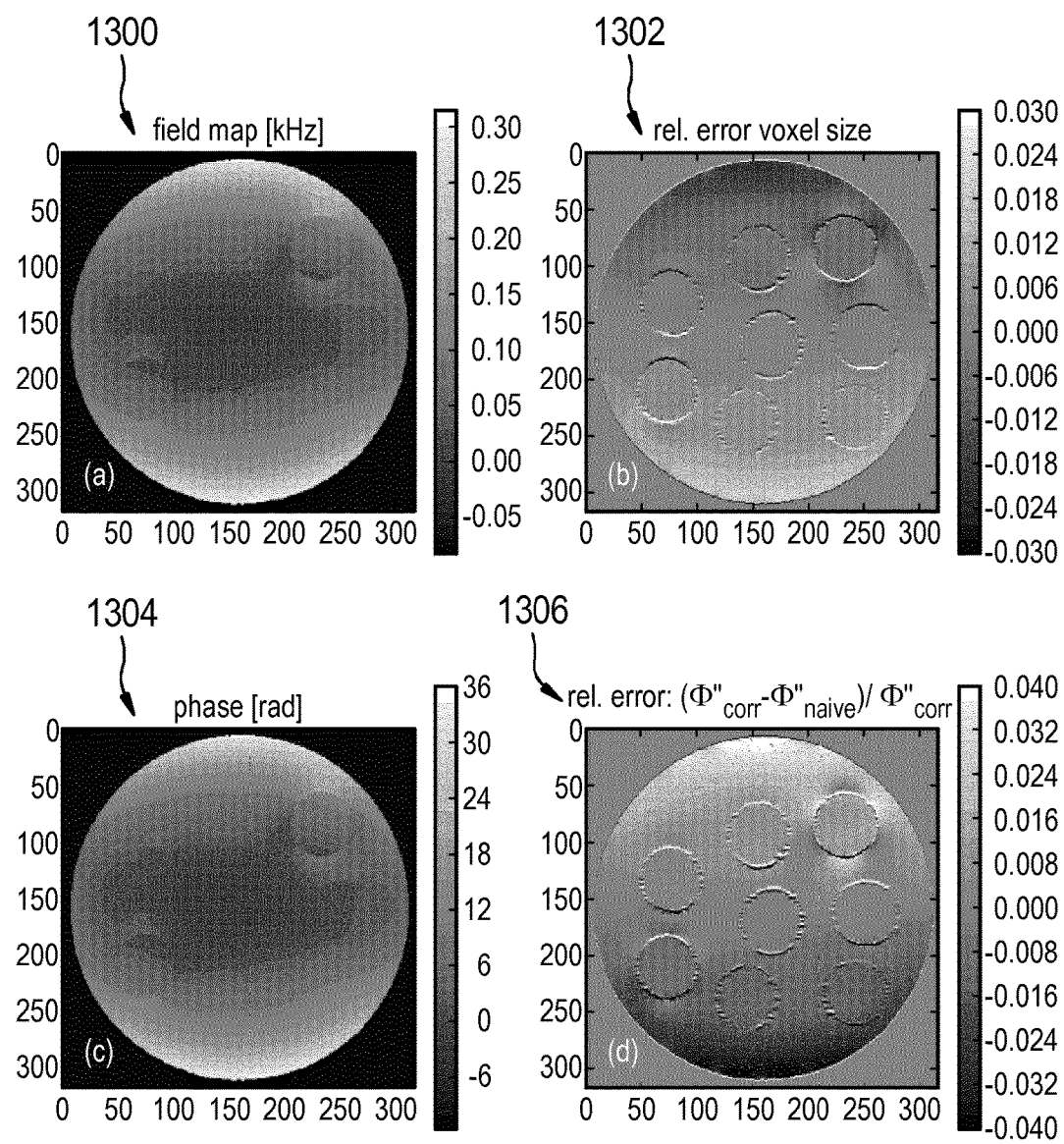
FIG. 13 shows four images.

FIG. 13 shows four images 1300, 1302, 1304, and 1306. The first image 1300 shows an axial slice of a phantom showing the measurement of the field map. Image 1302 shows the relative error of the voxel size for the voxels shown in image 1300. The third image 1304 shows the phase of the image 1300 at the echo time of 19.4 ms. The fourth image 1306 shows the relative error of the second derivative of the phase. In all four images the vertical axis is in the readout direction.

Figure 14:
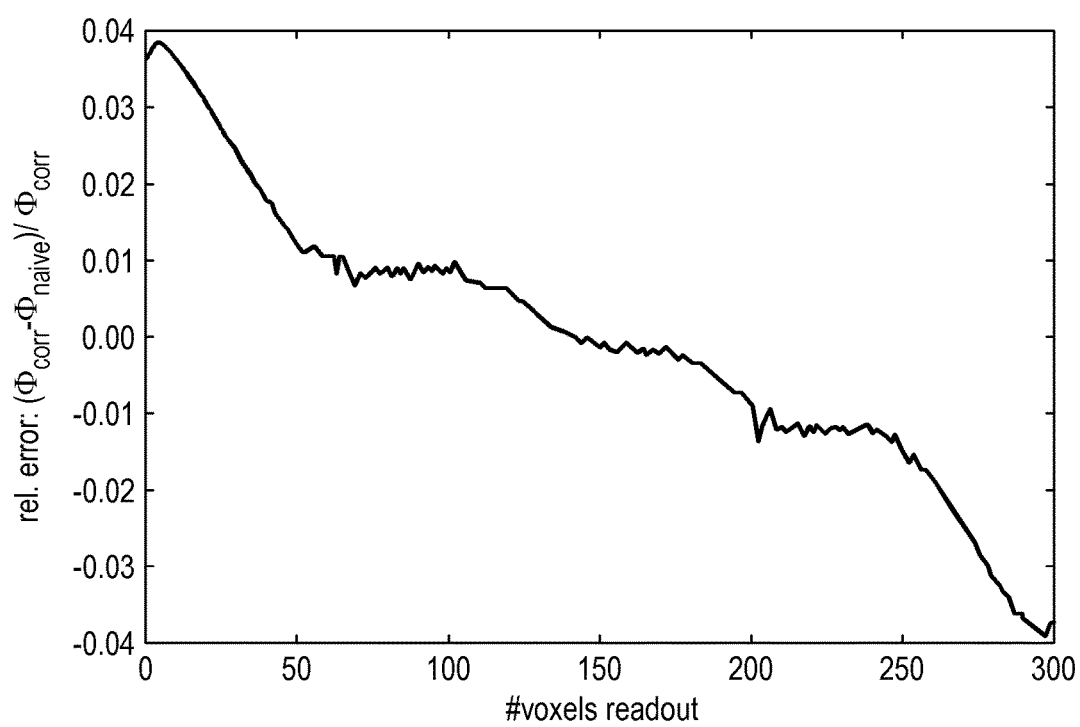
FIG. 14 shows a plot of the relative error of the second derivative of the phase along the readout direction which is averaged over 10 voxels along the x-direction in one slice for an experiment.

FIG. 14 shows a plot of the relative error of the second derivative of the phase along the readout direction which is averaged over 10 voxels along the x-direction in one slice.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 magnetic resonance system
104 magnet
106 bore of magnet
108 measurement zone or imaging zone
110 magnetic field gradient coils
112 magnetic field gradient coil power supply
114 radio-frequency coil
116 transceiver
118 subject
120 subject support
122 actuator
125 slices
126 computer system
128 hardware interface
130 processor
132 user interface
134 computer storage
136 computer memory
140 Dixon pulse sequence data
142 magnetic resonance data
144 fat image
146 water image
148 B0 inhomogeneity map
150 estimated B1 phase map
152 zero echo time B1 phase map
154 at least one electrical conductivity map
156 fat region location data
158 water region location data
160 control module
162 image reconstruction module
164 image processing module
166 differential equation kernel module
200 acquire magnetic resonance data by controlling the magnetic resonance imaging system using the Dixon pulse sequence data
202 estimate a B0 inhomogeneity map and estimate an estimated B1 phase map by analyzing the magnetic resonance data according to an n-point Dixon method
204 calculate a zero echo time B1 phase map by interpolating the estimated B1 phase map to an echo time of zero using the B0 inhomogeneity map
206 calculate at least one calculated electrical conductivity map using the zero echo time B1 phase map
300 magnetic resonance imaging system.
302 antenna
304 radio-frequency transmitter
306 target zone
310 estimated permittivity map
312 treatment plan
314 heating system control commands
316 heating system control generation module
400 water region
402 fat region
1000 boundary region
1100 magnetic resonance system
1102 pulse sequence data
1104 magnetic resonance data
1106 B1 amplitude map
1108 corrected voxel size
1110 second derivative 1200 acquire the magnetic resonance data by controlling the magnetic resonance imaging system with pulse sequence data 1202 calculate a B0 inhomogeneity map by analyzing the magnetic resonance data according to the magnetic resonance imaging method 1204 calculate a B1 phase map and/or a B1 amplitude map by analyzing the magnetic resonance data according to the magnetic resonance imaging method 1206 calculate a second derivative of the B1 phase map and/or a second derivative of the B1 magnitude map and/or a second derivative of the B0 inhomogeneity map in at least one predetermined direction 1300 magnetic resonance image of a phantom which shows an axial slice of a phantom showing the measurement of the field map.

1302 magnetic resonance image of a phantom which shows the relative error of the voxel size for the voxels shown in FIG. 1300.

1304 magnetic resonance image of a phantom which shows the phase of the image 1300 at the echo time of 19.4 ms.

1306 magnetic resonance image of a phantom which shows the relative error of the second derivative of the phase. In all four images the vertical axis is in the readout direction.

The invention claimed is:

1. A magnetic resonance imaging system for acquiring magnetic resonance data from a subject within an imaging zone, wherein the magnetic resonance imaging system comprises:

a memory for storing machine executable instructions and pulse sequence data, wherein the pulse sequence data comprises instructions for controlling the magnetic resonance imaging system to acquire magnetic resonance data according to a magnetic resonance imaging method; ; wherein the pulse sequence data comprises a multi-echo pulse sequence for measuring a B0 map, wherein the pulse sequence data comprises B0 mapping pulse sequence data, and wherein any one of the following:

the pulse sequence data further comprises a B1 magnitude measuring pulse sequence for measuring a B1 magnitude map, and wherein the pulse sequence data comprises B1 magnitude mapping pulse sequence data, the pulse sequence data further comprises a B1 phase measuring pulse sequence for measuring a B1 phase map, wherein the pulse sequence data comprises B1 phase mapping pulse sequence data, and combinations thereof, a processor for controlling the magnetic resonance imaging system, wherein execution of the machine executable instructions causes the processor to:

acquire the magnetic resonance data by controlling the magnetic resonance imaging system with the pulse sequence data;

calculate a B0 inhomogeneity map by analyzing the magnetic resonance data according to the magnetic resonance imaging method, calculate a B1 phase map and/or a B1 amplitude map by analyzing the magnetic resonance data according to the magnetic resonance imaging method; and calculate a second derivative of the B1 phase map and/or a second derivative of the B1 magnitude map and/or a second derivative of the B0 inhomogeneity map in at least one predetermined direction, wherein the second derivative is calculated using a corrected voxel size in the at least one predetermined direction, wherein the corrected voxel size is calculated using a correction factor calculated from a derivative of the B0 inhomogeneity map.

2. The magnetic resonance imaging system of claim 1, wherein execution of the machine executable instructions further cause the processor to calculate a zero echo time B1 phase map by interpolating the B1 phase map to an echo time of zero using the B0 inhomogeneity map, and wherein the second derivative of the B1 phase map is calculated using the zero echo time B1 phase map.

3. The magnetic resonance imaging system of claim 1, wherein the pulse sequence data is Dixon pulse sequence data, wherein the magnetic resonance imaging method is an n-point Dixon method, wherein n is equal to or greater than 2, wherein the B0 inhomogeneity map and the B1 phase map are estimated by analyzing the magnetic resonance data according to the n-point Dixon method.

4. The magnetic resonance imaging system of claim 3, wherein execution of the machine executable instructions further causes the processor to:

calculate a fat image and a water image when analyzing the magnetic resonance data according to the n-point Dixon method, identify fat regions within the subject by segmenting the fat image, identify water regions within the subject by segmenting the water image; and calculate an estimated electrical conductivity map and/or an estimated permittivity map using the fat regions and the water regions.

5. The magnetic resonance imaging system of claim 4, wherein the magnetic resonance imaging system further comprises an electromagnetic tissue heating system, wherein execution of the machine executable instructions further causes the processor to estimate spatially dependent heating of the subject using the estimated permittivity map, wherein execution of the machine executable instructions further causes the processor to further estimate the heating of the subject using the estimated electrical conductivity map and/or the at least one calculated electrical conductivity map.

6. The magnetic resonance imaging system of claim 1, wherein the multi-echo pulse sequence comprises instructions for controlling the magnetic resonance imaging system to acquire magnetic resonance data according to any one of the following magnetic resonance imaging methods: an n-point Dixon method and a multi-echo pulse sequence method.

7. The magnetic resonance imaging system of claim 1, wherein the B1 magnitude measuring pulse sequence comprises instructions for controlling the magnetic resonance imaging system to acquire magnetic resonance data according to any one of the following magnetic resonance imaging methods: an Actual Flip-Angle Imaging (AFI) magnetic resonance imaging method, a Dual Refocusing Echo Acquisition Mode (DREAM) magnetic resonance imaging method, and a Bloch-Siegert shift magnetic resonance imaging method.

8. The magnetic resonance imaging system of claim 1, wherein the B1 phase measuring pulse sequence comprises instructions for controlling the magnetic resonance imaging system to acquire magnetic resonance data according to any one of the following magnetic resonance imaging methods: a spin echo based magnetic resonance imaging method and a balanced gradient echo magnetic resonance imaging method.

9. The magnetic resonance imaging system of claim 1, wherein execution of the machine executable instructions further causes the processor to calculate at least one calculated electrical conductivity map using the second derivative of the B1 phase map in the at least one predetermined direction.

10. The magnetic resonance imaging system of claim 1, wherein execution of the machine executable instructions further causes the processor to calculate at least one susceptibility map using the second derivative of the B0inhomogeneity map in at least one predetermined direction according to a quantitative susceptibility mapping method.

11. The magnetic resonance imaging system of claim 1, wherein the pulse sequence data specifies a readout gradient for each of the at least one predetermined direction, wherein the corrected voxel size in each of the at least one predetermined direction is:

$$dx_{true}(\vec{r}) = dx_{nominal}\left(1 + \frac{f'(\vec{r})}{\gamma G_R}\right),$$

wherein x is one of the at least one predetermined direction, wherein $\vec{r}$ is a location of a voxel, wherein $dx_{nominal}$ is an nominal voxel size in the one of the at least one predetermined direction, wherein $f'(\vec{r})$ is a derivative of the B0inhomogeneity map in the one of the at least one predetermined direction, wherein $\gamma$ is the gyromagnetic ratio, and wherein $G_R$ is the strength of the readout gradient in the one of the at least one predetermined direction.

12. The magnetic resonance imaging system of claim 11, wherein the second derivative of MR phase image reconstructed from the magnetic resonance data is:

$$\Phi''(\vec{r}) = \frac{\Phi(x - dx_{nominal}) - 2\Phi(x) + \Phi(x + dx_{nominal})}{dx_{true}(\vec{r})^2},$$

wherein $\Phi$ is any one of the following: the B1 phase map, the B1 magnitude map, and the B0 inhomogeneity map.

13. A method of operating a magnetic resonance imaging system for acquiring magnetic resonance data from a subject within an imaging zone,
wherein the method comprises the steps of:
acquiring the magnetic resonance data by controlling the magnetic resonance imaging system with pulse sequence data, wherein the pulse sequence data comprises instructions for controlling the magnetic resonance imaging system to acquire magnetic resonance data according to a magnetic resonance imaging method; wherein the pulse sequence data comprises a multi-echo pulse sequence for measuring a B0 map, wherein the pulse sequence data comprises B0 mapping pulse sequence data, and wherein any one of the following:
the pulse sequence data further comprises a B1 magnitude measuring pulse sequence for measuring a B1 magnitude map, and wherein the pulse sequence data comprises B1 magnitude mapping pulse sequence data,
the pulse sequence data further comprises a B1 phase measuring pulse sequence for measuring a B1 phase map, wherein the pulse sequence data comprises B1 phase mapping pulse sequence data, and combinations thereof,
calculating a B0 inhomogeneity map by analyzing the magnetic resonance data according to the magnetic resonance imaging method;
calculating the B1 phase map and/or a B1 amplitude map by analyzing the magnetic resonance data according to a magnetic resonance imaging method; and
calculating a second derivative of the B1 phase map and/or a second derivative of the B1 magnitude map and/or a second derivative of the B0 inhomogeneity map in at least one predetermined direction, wherein the second derivative is calculated using a corrected voxel size in the at least one predetermined direction, wherein the corrected voxel size is calculated using a correction factor calculated from a derivative of the B0 inhomogeneity map.

14. A computer program product comprising machine executable instructions for execution by a processor controlling a magnetic resonance imaging system for acquiring magnetic resonance data from a subject within an imaging zone, wherein execution of the machine executable instructions causes the processor to:
acquire the magnetic resonance data by controlling the magnetic resonance imaging system with the pulse sequence data, wherein the pulse sequence data comprises instructions for controlling the magnetic resonance imaging system to acquire magnetic resonance data according to a magnetic resonance imaging method; wherein the pulse sequence data comprises a multi-echo pulse sequence for measuring a B0 map, wherein the pulse sequence data comprises B0 mapping pulse sequence data, and wherein any one of the following:
the pulse sequence data further comprises a B1 magnitude measuring pulse sequence for measuring a B1 magnitude map, and wherein the pulse sequence data comprises B1 magnitude mapping pulse sequence data,
the pulse sequence data further comprises a B1 phase measuring pulse sequence for measuring a B1 phase map, wherein the pulse sequence data comprises B1 phase mapping pulse sequence data, and combinations thereof,
calculate a B0 inhomogeneity map by analyzing the magnetic resonance data according to the magnetic resonance imaging method;
calculate a B1 phase map and/or a B1 amplitude map by analyzing the magnetic resonance data according to the magnetic resonance imaging method; and
calculate a second derivative of the B1 phase map and/or a second derivative of the B1 magnitude map and/or a second derivative of the B0 inhomogeneity map in at least one predetermined direction, wherein the second derivative is calculated using corrected voxel size in the at least one predetermined direction, wherein the corrected voxel size is calculated using a correction factor calculated from the a derivative of the B0 inhomogeneity map.

* * * * *